(12) United States Patent
Du et al.

(10) Patent No.: US 11,994,675 B2
(45) Date of Patent: May 28, 2024

(54) HEAD-MOUNTED DEVICE FOR TRACKING SCREEN TIME

(71) Applicant: GOOGLE LLC, Mountain View, CA (US)

(72) Inventors: Ruofei Du, San Francisco, CA (US); Maksym Dzitsiuk, San Leandro, CA (US)

(73) Assignee: GOOGLE LLC, Mountain View, CA (US)

( * ) Notice: Subject to any disclaimer, the term of this patent is extended or adjusted under 35 U.S.C. 154(b) by 0 days.

(21) Appl. No.: 17/663,444

(22) Filed: May 16, 2022

(65) Prior Publication Data

US 2023/0367116 A1 Nov. 16, 2023

(51) Int. Cl.
*G02B 27/00* (2006.01)
*G08B 25/01* (2006.01)
*G02B 27/01* (2006.01)

(52) U.S. Cl.
CPC ....... *G02B 27/0093* (2013.01); *G08B 25/016* (2013.01); *G02B 2027/014* (2013.01); *G02B 2027/0178* (2013.01)

(58) Field of Classification Search
CPC ............................ G02B 27/0093; G08B 25/016
See application file for complete search history.

(56) References Cited

U.S. PATENT DOCUMENTS

| | | | | |
|---|---|---|---|---|
| 9,898,082 | B1 * | 2/2018 | Greenwald | G06F 3/013 |
| 10,429,656 | B1 * | 10/2019 | Sharma | G02B 17/023 |
| 10,429,657 | B1 * | 10/2019 | Sharma | G02B 27/0172 |
| 10,429,927 | B1 * | 10/2019 | Sharma | G06F 3/0346 |
| 10,610,775 | B1 * | 4/2020 | Ebert | G06F 3/013 |
| 2012/0120070 | A1 | 5/2012 | Baillot | |
| 2014/0292637 | A1 | 10/2014 | Peng et al. | |
| 2018/0299953 | A1 * | 10/2018 | Selker | G06F 3/0346 |

(Continued)

FOREIGN PATENT DOCUMENTS

WO 2021212227 A1 10/2021

OTHER PUBLICATIONS

Rooksby, et al., "Personal Tracking of Screen Time on Digital Devices", Behavioral Change; #chi4goog, CHI 2016, San Jose, CA, USA, 2016, pp. 284-296.

(Continued)

*Primary Examiner* — Chun-Nan Lin
(74) *Attorney, Agent, or Firm* — Brake Hughes Bellermann LLP (57) ABSTRACT

A head-mounted device, such as augmented reality glasses, can be configured to track screen time. The head-mounted device can advantageously track screen time across a variety of devices whether or not they are configured to such measurements. Various modes for tracking the screen time may be used based on accuracy, power consumption, and privacy. The head-mounted device may track in a mode based on a battery level, a device setting or a user input. The head-mounted device may accumulate screen times in a database and in some implementations, can link screen times with devices in the database based on device information gathered by the head-mounted device during the tracking process. The head-mounted device may be configured to generate and display an alert based on one or more rules about screen time.

20 Claims, 8 Drawing Sheets

(56) References Cited

U.S. PATENT DOCUMENTS

| | | |
|---|---|---|
| 2019/0221191 A1 | 7/2019 | Chhipa et al. |
| 2021/0081038 A1* | 3/2021 | Sengelaub ......... H04N 5/23245 |
| 2021/0103336 A1* | 4/2021 | Li .......................... G06V 40/20 |
| 2021/0201021 A1 | 7/2021 | Novelli et al. |

OTHER PUBLICATIONS

Vizcaino, et al., "Reliability of a New Measure to Assess Modern Screen Time in Adults", BMC Public Health; https://bmcpublichealth.biomedcentral.com/articles/10.1186/s12889-019-7745-6, Jan. 5, 2022, 24 pages.

Invitation to Pay Additional Fees for PCT Application No. PCT/US2023/021157, dated Jul. 28, 2023, 16 pages.

Fletcher, et al., "Wearable Sensor and Algorithm for Automated Measurement of Screen Time", IEEE, 2016, pp. 109-116.

Kaluarachchi, et al., "Eyeknowyou: A DIY Toolkit to Support Monitoring Cognitive Load and Actual Screen Time Using a Head-Mounted Webcam", Adjunct Proceedings of the 2022 Nordic Human-Computer Interaction Conference, ACMPUB27; https://doi.org/10.1145/3447527.3474850, Sep. 27, 2021, 8 pages.

* cited by examiner

HEAD-MOUNTED DEVICE FOR TRACKING SCREEN TIME

FIELD OF THE DISCLOSURE

The present disclosure relates to head-mounted devices and more specifically to a head-mounted device configured to measure screen time across multiple devices.

BACKGROUND

Screen time is an amount of time a person spends using a device with a screen. Extensive screen time may negatively affect sleep, physical health, brain development, and/or behavior.

SUMMARY

In some aspects, the techniques described herein relate to a head-mounted device including: an eye-tracking camera directed at an eye of a user; and a processor in communication with the eye-tracking camera, the processor configured by instructions to: capture an eye image of the eye of the user using the eye-tracking camera; analyze the eye image to identify a screen reflection; start a screen timer after the screen reflection is identified; periodically capture subsequent eye images to track the screen reflection over time; stop the screen timer when the screen reflection can no longer be tracked; and record a screen time of a first instance based on the screen timer.

In some aspects, the techniques described herein relate to a head-mounted device, wherein analyzing the eye image to identify a screen reflection is performed by a neural network.

In some aspects, the techniques described herein relate to a head-mounted device, wherein the processor is further configured to: classify the screen time of the first instance as for a first device based on a machine learning model configured by device information captured by the head-mounted device; and record the screen time of the first instance for the first device in a database.

In some aspects, the techniques described herein relate to a head-mounted device, wherein the device information is any combination of a device identifier, a content of the screen reflection, a characteristic of the screen reflection, and a location of the user.

In some aspects, the techniques described herein relate to a head-mounted device, wherein the processor is further configured by instructions to: detect that a mode of the head-mounted device for screen-time tracking is a lower-power mode.

In some aspects, the techniques described herein relate to a head-mounted device, further including: a front-facing camera, and wherein: the processor is further configured to: detect that the mode of the head-mounted device for screen-time tracking is a higher-power mode: capture a field-of-view image of a field-of-view of the user using the front-facing camera; analyze the field-of-view image to identify a screen; start the screen timer after the screen is identified in the field-of-view image; periodically capture subsequent field-of-view images to track the screen over time; stop the screen timer when the screen can no longer be tracked; and record a screen time of a second instance based on the screen timer.

In some aspects, the techniques described herein relate to a head-mounted device, further including: at least one orientation sensor configured to sense orientation data of the head-mounted device; and at least one location sensor configured to sense a relative location data of a device, and wherein: the processor is further configured to: detect that the mode of the head-mounted device for screen-time tracking is a no-camera mode for screen-time tracking; and in the no-camera mode, the processor is configured to: capture the orientation data of the head-mounted device and the relative location data of the device; analyze the orientation data and the relative location data to identify a viewing condition; start the screen timer after the viewing condition is identified; periodically capture subsequent orientation data and subsequent relative location data to track the viewing condition over time; stop the screen timer when the viewing condition can no longer be tracked; and record a screen time of a third instance based on the screen timer.

In some aspects, the techniques described herein relate to a head-mounted device, wherein: the at least one orientation sensor includes an inertial measurement unit (IMU); and the at least one location sensor includes an ultra-wideband (UWB) sensor.

In some aspects, the techniques described herein relate to a head-mounted device, wherein the processor is further configured to: generate an alert based on the screen time of the first instance, the screen time of the second instance and/or the screen time of the third instance; and display the alert on a display of the head-mounted device.

In some aspects, the techniques described herein relate to a computer-implemented method, including: detecting that a mode of a head-mounted device for screen-time tracking is a lower-power mode; capturing an eye image of an eye using an eye-tracking camera of the head-mounted device; analyzing the eye image to identify a screen reflection; starting a screen timer after the screen reflection is identified; periodically capturing subsequent eye images to track the screen reflection over time; and stopping the screen timer when the screen reflection can no longer be tracked.

In some aspects, the techniques described herein relate to a computer-implemented method, wherein periodically capturing subsequent eye images to track the screen reflection over time includes: repeating the capturing and the analyzing at a cycle period that is greater than 2 seconds.

In some aspects, the techniques described herein relate to a computer-implemented method, wherein detecting that the mode of the head-mounted device for screen-time tracking is a lower-power mode includes: detecting a battery level of the head-mounted device; and determining that the battery level is below a threshold.

In some aspects, the techniques described herein relate to a computer-implemented method, wherein analyzing the eye image to identify a screen reflection includes: applying the eye image to an input of a neural network, the eye image including the eye and the screen reflection; and receiving a screen image at an output of the neural network, the screen image including the screen reflection.

In some aspects, the techniques described herein relate to a computer-implemented method, further including: detecting that the mode of the head-mounted device for screen-time tracking is a higher-power mode; capturing a field-of-view image using a front facing camera of the head-mounted device; analyzing the field-of-view image to identify a screen; starting the screen timer after the screen is identified; periodically capturing subsequent field-of-view images to track the screen over time; and stopping the screen timer when the screen can no longer be tracked.

In some aspects, the techniques described herein relate to a computer-implemented method, wherein detecting that the mode of the head-mounted device for screen-time tracking is a higher-power mode includes: detecting a battery level of the head-mounted device; and determining that the battery level is above a threshold.

In some aspects, the techniques described herein relate to a computer-implemented method, further including: detecting that the mode of the head-mounted device for screen-time tracking is a no camera mode; capturing orientation data of the head-mounted device using at least one orientation sensor of the head-mounted device; capturing relative location data of a device from an ultra-wideband (UWB) signal received at the head-mounted device; analyzing the orientation data and the relative location data to determine a viewing condition; starting a screen timer after the viewing condition is identified; periodically capturing subsequent orientation data and relative location data to track the viewing condition over time; and stopping the screen timer when the viewing condition can no longer be tracked.

In some aspects, the techniques described herein relate to a computer-implemented method, further including: recording a screen time in a database based on the screen timer; and generating an alert when the screen time satisfies a criterion.

In some aspects, the techniques described herein relate to a computer-implemented method, further including: classifying instances of screen times as corresponding to devices based on device information captured by the head-mounted device.

In some aspects, the techniques described herein relate to a head-mounted device including: an eye-tracking camera directed at an eye of a user; a front-facing camera directed at a field-of-view of the user; at least one orientation sensor configured to sense orientation data of the head-mounted device worn by the user; and a processor configured by instructions to: detect a lower-power mode based on a battery level of the head-mounted device, wherein in the lower-power mode: screen-time for a device is determined based on eye images from the eye-tracking camera applied to a neural network; and detect a higher-power mode based on the battery level of the head-mounted device wherein in the higher-power mode: screen-time for the device is determined based on images from the front-facing camera applied to an image-recognition algorithm.

In some aspects, the techniques described herein relate to a head-mounted device, wherein the processor is further configured by instructions to: detect a no-camera mode based on a user input, wherein in the no-camera mode: screen-time for the device is based on the orientation data of the head-mounted device and relative location data of the device, captured from an ultra-wideband (UWB) signal received at the head-mounted device and applied to a machine learning model.

In some aspects, the techniques described herein relate to a head-mounted device, wherein the head-mounted device is augmented-reality glasses (i.e., AR glasses).

The foregoing illustrative summary, as well as other exemplary objectives and/or advantages of the disclosure, and the manner in which the same are accomplished, are further explained within the following detailed description and its accompanying drawings.

BRIEF DESCRIPTION OF THE DRAWINGS

The components in the drawings are not necessarily to scale relative to each other. Like reference numerals designate corresponding parts throughout the several views.

DETAILED DESCRIPTION

It may be desirable to measure a total screen time for a person during a period; however, accurately measuring the total screen time for the person may not be practical when the person uses multiple devices. For example, during the course of a day, a person may view a movie on a television, play a video game on a computer, read a book on a tablet, and video chat on a mobile phone. While one or more of these devices may be configured to record (i.e., measure) screen time, there is not a way to measure and tally screen time across multiple devices for a variety of reasons. For example, some of the devices may not be able to easily exchange screen time information due to different operating systems, while other devices may not be able to measure or communicate this information at all (e.g., older televisions).

The present disclosure addresses the technical problem of measuring and recording (i.e., tracking) screen times across multiple devices through the use of a head-mounted device configured to monitor a user to determine times when the user is engaged with a screen of a device and to compute a screen time for the device based on these times. The head-mounted device may be further configured to track a plurality of screen times for each of the plurality of devices. Additionally, the head-mounted device may be configured to combine screen times for devices to measure a total screen time for a person. Additionally, the head-mounted device may be configured to take an action when a screen time of one or more or the devices satisfies a criterion. For example, the criterion may be a threshold related to a maximum screen time over a period and the action may be related to limiting the screen time for the user. The criterion and the period are configurable and can suit a variety of applications.

Screen time tracking may require regular measurements using the head-mounted device. The regular measurements may consume power, which can limit a use time for a head-mounted device. For example, augmented reality glasses (i.e., AR glasses) may have a limited power budget because of a smaller battery size. As a result, regular screen time tracking can pose a technical problem of consuming more power than practical for a head-mounted device. The present disclosure further addresses the technical problem of power consumption associated with screen time measurements by disclosing a multi-mode approach, where each mode has a different power consumption. Selecting the mode of screen-time tracking can be based on a power condition of the head-mounted device. For example, a screen-time tracking mode that consumes less power may be selected in a low battery condition to extend an operating time for the head-mounted device. Additionally, the multi-mode approach may allow for additional modes that can have added benefits to a user. For example, a non-imaging mode for tracking screen time is disclosed, which may enhance a privacy of the user.

A user may fail to recognize their accumulated screen time over a period. For example, a user may become so distracted by screen content that they fail to realize how long they have been observing a screen. The present disclosure further addresses the need for alerting a user of screen time. For example, when the total screen time across devices reaches an amount, then the head-mounted device may be configured to generate an alert and/or temporarily limit a function of a device. These actions may help prevent or mitigate symptoms associated with the overuse of the devices and can help a user conform to rules regarding screen time. Further, these actions may help a user or someone responsible for the user (e.g., parent, manager) generally understand their behavior regarding screen time. For example, screen time tracking can be used to verify engagement (e.g., tracking a user's work).

Figure 1:
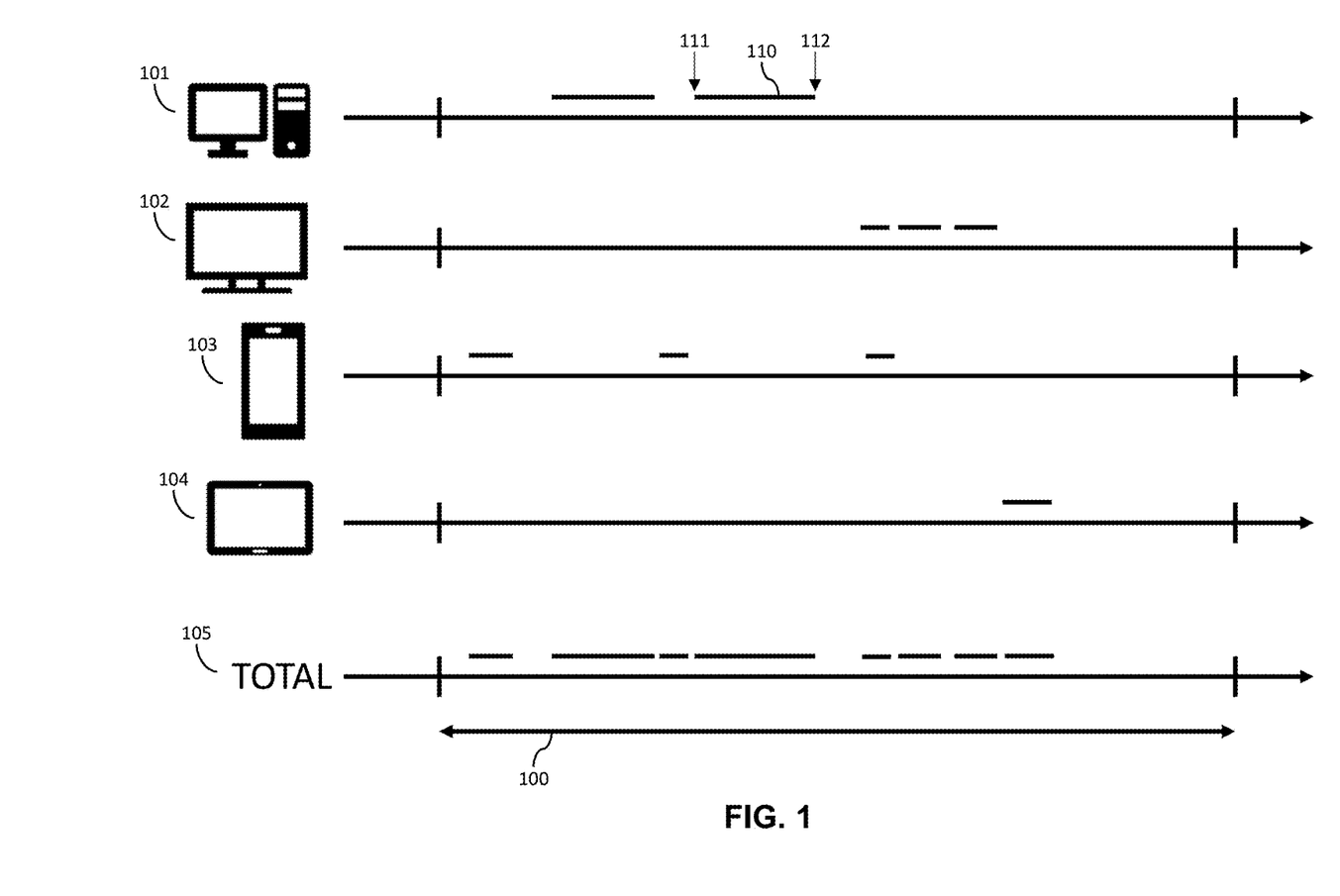
FIG. 1 graphically illustrates screen times for a user over a period according to a possible implementation of the present disclosure.

FIG. 1 graphically illustrates screen times for a plurality of devices. The screen time for each device is plotted on a timeline for a period (e.g., 24 hours). The screen times are shown as lines for each instance of screen engagement, and the length of each line corresponds to a screen time for the device. For example, an instance 110 of screen time for the desktop computer is shown in the first graph 101. The screen time for the instance 110 may be computed as the time elapsed between a beginning 111 (i.e., START) of the instance 110 and an end 112 (i.e., STOP) of the instance 110. The accumulated screen time for all devices (i.e., across devices) is also plotted as a total screen time for the period 100. The graphs are presented to help understanding. It should be understood that the devices and screen times illustrated are hypothetical and represent one possible implementation of many possible variations. For example, screen times for additional and/or different devices may be included.

As shown, a first graph 101 illustrates instances of screen time corresponding to a first device (i.e., desktop computer), a second graph 102 illustrates instances of screen time corresponding to a second device (i.e., television), a third graph 103 illustrates instances of screen time associated with a third device (i.e., mobile phone), and a fourth graph 104 illustrates instances of screen time associated with a fourth device (i.e., tablet). A fifth graph 105 illustrates the instances of screen time for all the devices (i.e., across all devices). The instances of screen time may be totaled to compute a total screen time for a period.

The total screen time may be computed in a variety of ways. In a possible implementation, the total screen time may be computed as a running total of accumulated screen time. In another possible implementation, the total screen time may be a sum of all the instances of screen time measured during the period. Accordingly, the screen time may be measured as a time (e.g., minutes) or as a rate (e.g., minutes/period).

In a possible implementation measuring screen time may include a screen timer. For example, a screen timer can be started and stopped for each instance of screen time during the period. The screen timer can then be reset when the period ends and re-started at the beginning of a subsequent period. The period 100 may be configured by a user (e.g., parent) or factory set based on a requirement (e.g., health guideline). The period 100 may also be adjustable. For example, the period may end when a total screen time is reached. For example, screen time may be accumulated until it reaches a threshold value, at which point the period ends.

The total screen time tracking may be customized to compute a running total of screen times based on devices, periods (e.g., times of day), and/or locations. For example, at time corresponding to a workday, a screen time for a work device of the user can be tracked, and in a possible implementation, a daily, weekly, or monthly total screen time for the work device may be computed. Further, a period corresponding to a particular screen-time tracking may be triggered based on a location of the head-mounted device (i.e., user). For example, when the user arrives at a location corresponding to work, a period corresponding to the workday may begin. A user based on devices, times, and/or locations.

Figure 2:
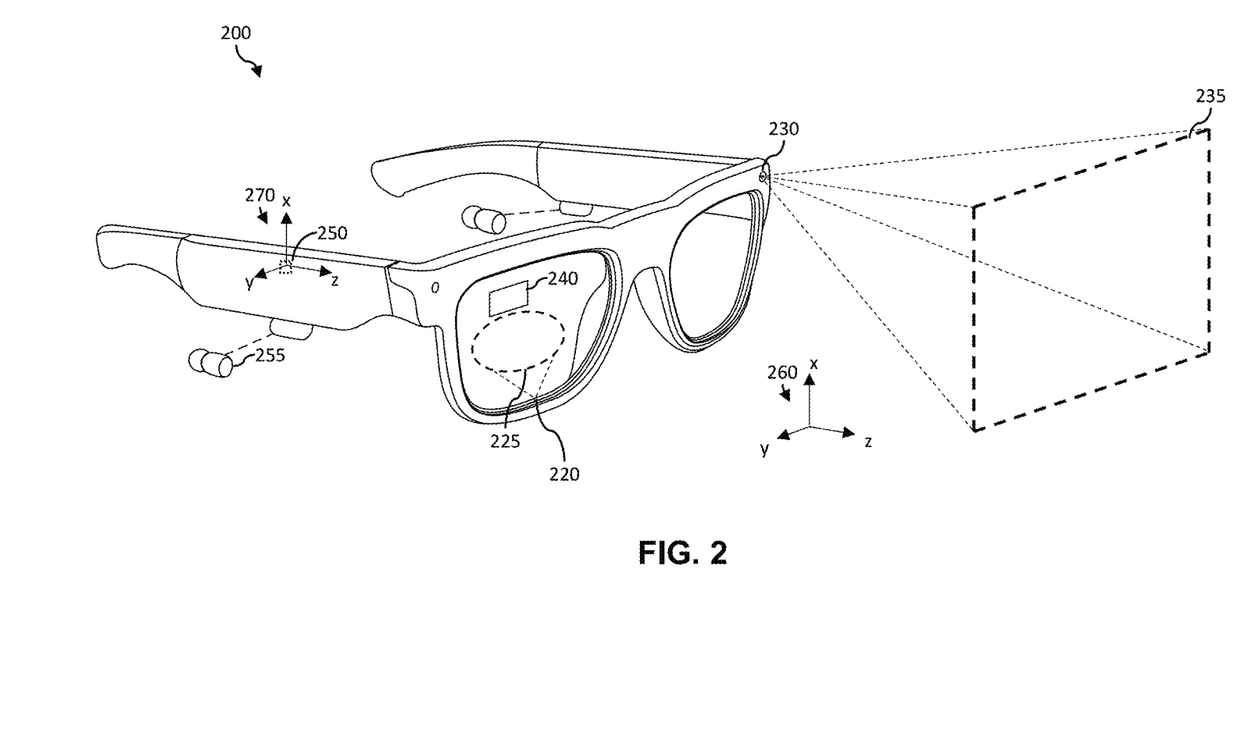
FIG. 2 is a perspective view of a head-mounted device according to a possible implementation of the present disclosure.

FIG. 2 is a perspective view of a head-mounted device according to a possible implementation of the present disclosure. As shown, the head-mounted device 200 may be implemented as smart glasses (e.g., AR glasses) configured to be worn on a head of a user. The head-mounted device 200 includes a left lens and a right lens coupled to the ears of a user by a left arm and a right arm, respectively. The user (i.e., wearer) may view the world through the left lens and the right lens, which are coupled together by a bridge configured to rest on the nose of the wearer.

The head-mounted device 200 may include sensing devices configured to help determine where a focus of a user is directed. For example, the head-mounted device 200 may include at least one front-facing camera. The front-facing camera 230 can include an image sensor that can detect intensity levels of visible and/or near-infrared light (i.e., NIR light). The front-facing camera 230 may be directed towards a front field-of-view (i.e., front FOV 235) or can include optics to route light from the front FOV 235 to the image sensor. For example, the front-facing camera 230 may be positioned in a front surface of the head-mounted device and include at least one lens to create an image of a front field-of-view (front FOV 235) on the image sensor. The front FOV 235 may include all (or part) of a field-of-view of the user so that images or video of the world from a point-of-view (POV) of the user may be captured by the front-facing camera 230.

The head-mounted device 200 may further include at least one eye-tracking camera. The eye-tracking camera 220 may be directed towards an eye field-of-view (i.e., eye-FOV 225) or can include optics to route light from the eye-FOV 225 to an eye-image sensor. For example, the eye-tracking camera 220 may be directed at an eye of a user and include at least one lens to create an image of the eye-FOV 225 on the eye-image sensor. The eye-FOV 225 may include all (or part) of a field of an eye of the user so that images or video of the eye. The images of the eyes may be analyzed by a processor of the head-mounted device (not shown) to determine where the user is looking. For example, a relative position of the pupil in an image of the eye may correspond to a gaze direction of the user.

The head-mounted device may further include at least one orientation sensor 250. The orientation sensor(s) may be implemented as a combination of accelerometers, gyroscopes, and magnetometers combined to form an inertial measurement unit (i.e., IMU) to determine an orientation of a head-mounted device. The IMU may be configured to provide a plurality of measurements describing the orientation and motion of the head-mounted display. For example, the IMU may have 6 degrees of freedom (6-DOF) which can describe three translation movements (i.e., x-direction, y-direction, or z-direction) along axes of a world coordinate system 260 and can three rotation movements (i.e., pitch, yaw, roll) about the axes of the world coordinate system 260. Data from the IMU can be combined with information regarding the magnetic field of the Earth using sensor fusion to determine an orientation of a head-mounted device coordinate system 270 with respect to the world coordinate system 260. Information from the front-facing camera 230, the eye-FOV 225 and IMU 250 may be combined to determine where a focus of a user is directed, which can enable augmented-reality applications. The head-mounted display may further include interface devices for these applications as well.

The head-mounted device 200 may further include human interface subsystems configured to present information to a user. For example, the head-mounted device 200 may include a display that is configured to display information (e.g., text, graphics, image) in a display area 240 in one or both lenses. The display area may be all or part of the lens and may be visually clear or translucent so that when it is not in use the user can view through the display area. The head-mounted device 200 may further include one or more speakers (e.g., earbuds 255) configured to play sounds (e.g., voice, music, tones). The present disclosure describes systems and methods that configure the sensing devices and interface devices of the head-mounted device for screen time measurements and responses (e.g., alerts).

Figure 3:
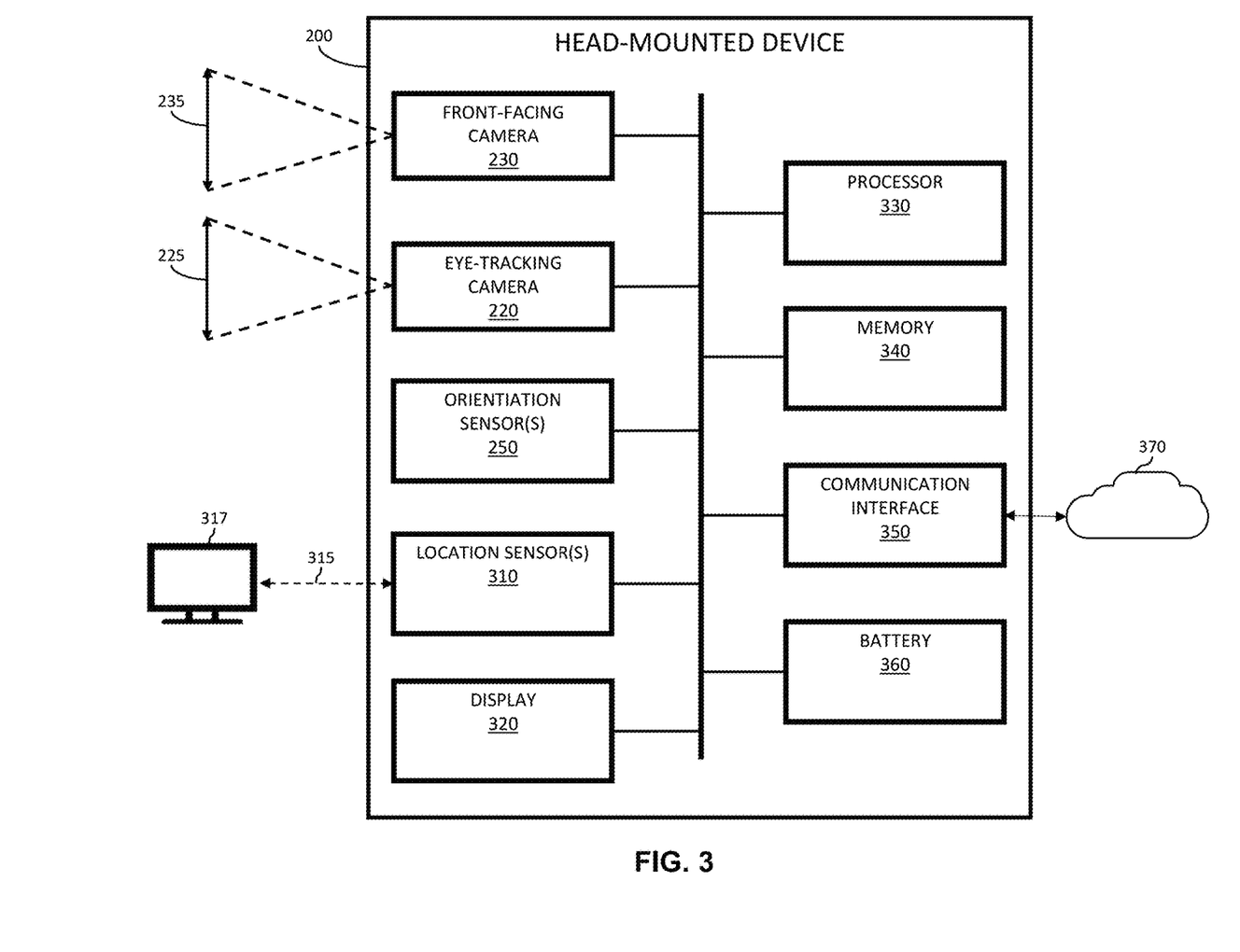
FIG. 3 is a system block diagram of a head-mounted device according to a possible implementation of the present disclosure.

FIG. 3 is a block diagram of a head-mounted device according to a possible implementation of the present disclosure. As discussed previously, the head-mounted device 200 includes a front-facing camera 230 directed at a point-of-view of the user and configured to capture images of a front FOV 235. The head-mounted device 200 further includes an eye-tracking camera 220 directed at an eye (or eyes) of the user and configured to capture images of an eye-FOV 225. The head-mounted device 200 further includes at least one orientation sensor 250 (e.g., IMU) configured to sense a movement, position and/or orientation of head of a person wearing the head-mounted device 200.

The head-mounted device 200 may further include at least one location sensor 310. The at least one location sensor may be configured to determine a location of the head-mounted device (i.e., of the user). The location sensor 310 may include an ultra-wideband (UWB) sensor. The location sensor 310 may be in communication with a screen device 317 over a communication link 315. For example, the head-mounted device 200 and the screen device 317 may exchange packets of information over a UWB communication link to determine the relative locations of the devices. For example, the location sensor may be configured to determine a round-trip time (RTT) for a packet to be communicated between the devices. A range between the head-mounted device and the screen device 317 may be sensed based on the round-trip time. Additionally, the location sensor may include multiple receivers configured to receive the packet communicated from the screen device 317. The location sensor may be configured to determine times of arrival of the packet at the receivers to determine an angle between the screen device 317 and the location sensor 310. The location sensor(s) may further include a global positioning system (GPS) sensor, which can be used to determine a geographic location of the head-mounted device (i.e., user). The geographic location may be further determined through a sensor fusion approach in which information from a local area network (e.g., WiFi network) and/or cellular network can further refine the geographic location.

The head-mounted device 200 further includes at least one processor 330. The processor is in communication with the cameras, sensors, and other modules and electronics of the head-mounted device. The processor is configured by instructions (e.g., software, application, etc.) to perform a multi-mode method for tracking screen times across devices. The instructions may be non-transitory computer readable instructions stored in, and recalled from, a memory 340. Alternatively, the instructions may be communicated to the processor from a computer coupled to a network 370 via a communication interface 350.

The processor 330 may be in communication with a battery 360. The processor 330 may be configured by instructions to monitor a level of the battery and determine a mode of the head-mounted device based on the level of the battery. For example, when the level of the battery is below a threshold, then it may be determined that the head-mounted device is in a lower-power mode, and when the level of the battery is above the threshold then it may be determined that the head-mounted device is in a higher-power mode.

The processor may be in communication with a display 320 of the head-mounted device 200. The processor 330 may be configured by instructions to transmit text, graphics, video, images, etc. to the display 320. For example, the processor 330 may be configured to present an alert to a user on the display 320 in response to the measured screen time.

Figure 4:
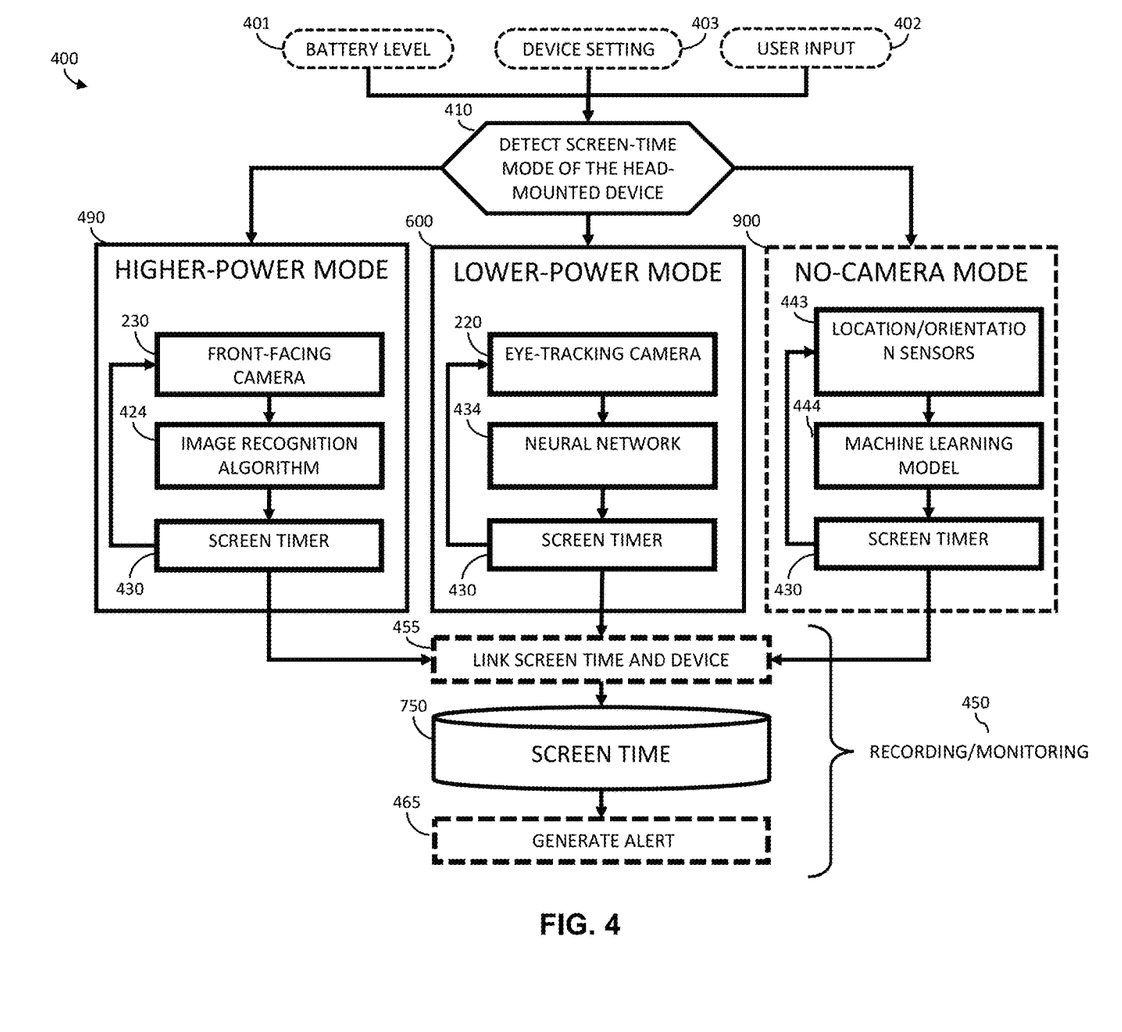
FIG. 4 is a flowchart illustrating a multi-mode screen-time tracking method according to a possible implementation of the present disclosure.

FIG. 4 is a flowchart of a multi-mode screen-time tracking method according to a possible implementation of the present disclosure. The method 400 includes detecting 410 a mode that the head-mounted device will use to measure screen time (i.e., a screen-time mode). Detecting the screen-time mode (i.e., mode) may be implemented in a variety of ways. In one possible implementation, detecting 410 the mode may include receiving an input from a user (i.e., user input 402) that specifies the mode. In another possible implementation, detecting 410 the mode may include receiving the mode from a device setting 403 of the head-mounted device, where the device setting (i.e. system setting) may be configurable by an application running on the head-mounted device. (e.g., AR application). In another possible implementation, detecting 410 the mode may include determining a mode based on a battery level 401 of the head-mounted device in an effort to balance a quality of the tracking with an operating time of the head-mounted device.

In a possible implementation, the detected mode may be a higher-power mode 490, a lower-power mode 600, or a no-camera mode 900. Each mode may have a different accuracy and power consumption. For example, the head-mounted device 200 may consume more power when it is the higher-power mode 490 than when it is in a lower-power mode 600. The higher-power mode 490 may generate screen times at a higher accuracy (i.e., a confidence) than the lower-power mode 600. The no-camera mode 900 may be used without any imaging, which can provide privacy to a user and provide the lowest power consumption of the modes. The no-camera mode 900 may be optional, however, because it can rely on position and orientation sensors that may or may not be present in all screen devices.

In a possible implementation, screen time tracking may alternate between the modes as required for either accuracy or battery life. For example, screen-time tracking for a device may begin in the higher-power mode 490 and then move to a lower-power mode 600 either between instances or within the same instance. This may help to recognize a device or a screen content at a beginning of an instance of screen time with a higher degree of confidence before moving to the lower-power mode, which can track the screen time more efficiently. In another example, a higher-power mode may be triggered when a screen is detected in a lower-power mode. This may help to increase accuracy only when it has been determined with some degree of confidence that a screen is being viewed.

As shown in the implementation of FIG. 4, the higher-power mode 490 uses the front-facing camera 230 of the head-mounted device and an image recognition algorithm 424 to determine the beginning (i.e., START) and end (i.e., STOP) of an instance of screen time. The lower-power mode 600 uses the eye-tracking camera 220 of the head-mounted device and a neural network 434 (e.g., U-net neural network) to determine the beginning/end of an instance of screen time. The no-camera mode 900 uses the location/orientation sensors 443 of the head-mounted device and a machine learning model (e.g., sensor fusion) to determine the beginning/end of an instance of screen time.

Each mode may trigger a screen timer 430 ON/OFF according to the START/STOP of the instance. In other words, the screen timer 430 may be used to determine screen time regardless of the mode used to determine the START/STOP of an instance of screen time. For example, the screen timer may be activated (i.e., started) when a screen is determined to be in view of a user and then deactivated (i.e., stopped) when a screen is determined to no longer be in view of the user. The determination of the screen viewing condition can be carried out differently depending on the mode. The screen timer 430 can be reset at the end of an instance. Alternatively, the screen timer 430 may be turned ON/OFF without resetting to accumulate screen time for a plurality of instances during a predetermined period and then reset at the end of the predetermined period.

As shown in FIG. 4, the method 400 may include a higher-power mode 490. The higher-power mode 490 uses the front-facing camera 230 of the head-mounted device, which consumes more power than the eye-tracking camera 220. In the lower-power mode 600, the front-facing camera 230 may be configured ON (i.e., enabled, powered, etc.) to capture an image or images that correspond to a field-of-view of the user. For example, the front-facing camera 230 captures video (e.g., high-resolution, color videos) of items in view of a user. The image (or images) may be analyzed by an image recognition algorithm 424 to identify (i.e., detect) a screen (or screens) being viewed by the user. The detection of the screen may trigger a screen timer 430 to start timing.

The higher-power mode 490 process described above may be repeated periodically (i.e., cycled) to track the screen in subsequently captured images to determine the screen time of an instance. Determining the screen time of an instance may include determining when the screen timer 430 should be stopped (i.e., deactivated, turned OFF). For example, when it has been determined that no screen has been detected in the images for a number of cycles, the screen timer may be turned OFF. Each cycle may be separated by a cycle period. For example, the higher-power mode 490 may be repeated with a cycle period of every few seconds (e.g., 2 seconds). When the instance has been concluded the screen timer may output a screen time of the instance for recording and/or monitoring.

As shown in FIG. 4, the method 400 may include a lower-power mode 600. The lower-power mode 600 uses the eye-tracking camera 220 of the head-mounted device, which consumes less power than the front-facing camera. In the lower-power mode 600, the eye-tracking camera 220 may be configured ON (i.e., enabled, powered, etc.) to capture an image or images that correspond to an eye (or eyes) of the user. For example, the eye-tracking camera 220 may capture video of the user's eye. An image of the eye may be analyzed by a neural network to detect a reflection and identify a screen in the reflection. The identification of the screen may trigger the screen timer 430 to start timing.

Figure 5:
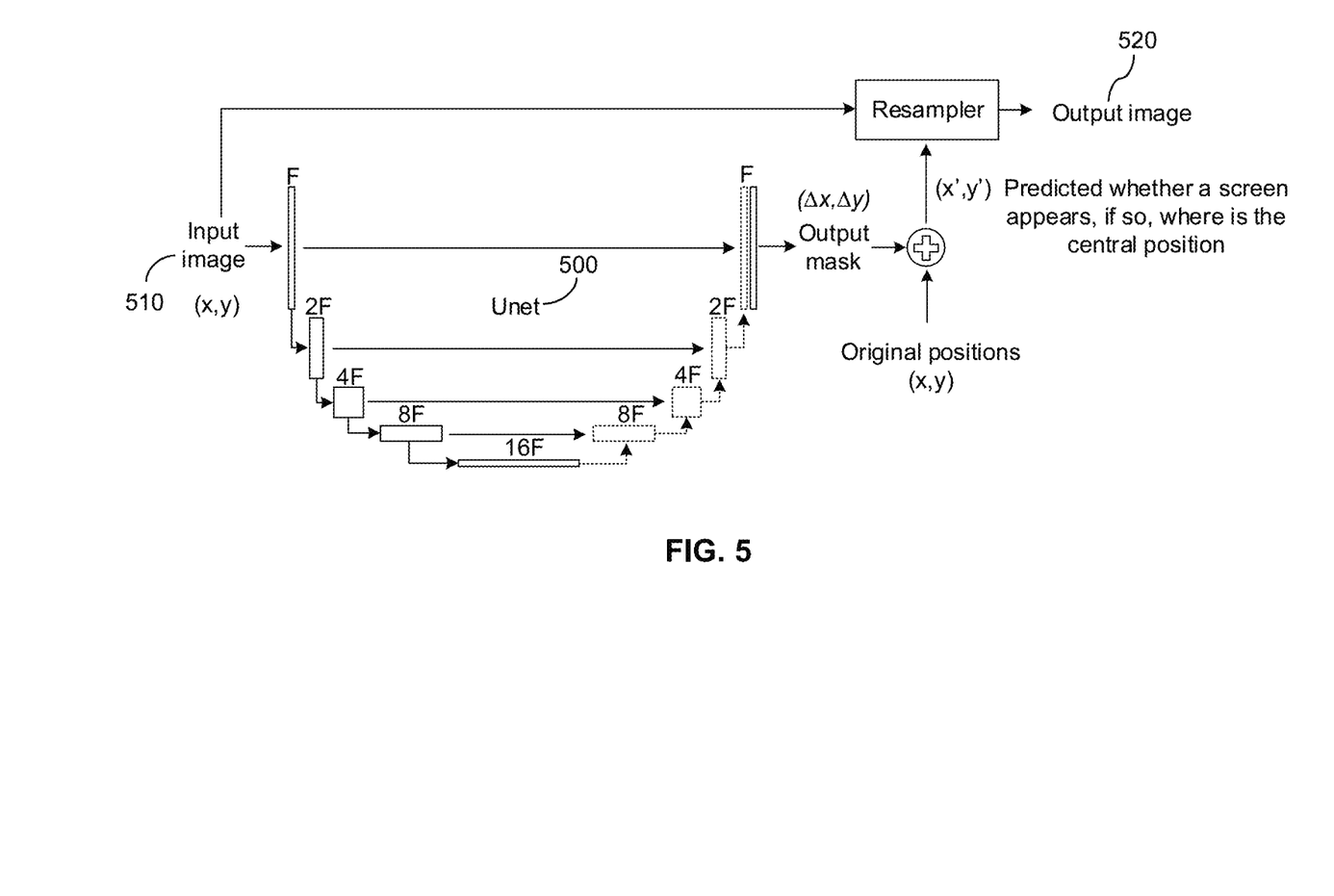
FIG. 5 is a block diagram of a possible neural network for a lower-power mode of the multi-mode screen time tracking method shown in FIG. 4.

FIG. 5 is a flowchart block diagram of a possible neural network for a lower-power mode of the multi-mode screen time tracking method shown in FIG. 4. The neural network is a U-net neural network 500 configured to receive an eye image 510 (i.e. input image) from the eye-tracking camera 220. The U-net neural network 500 may be configured to detect a reflection of the image of the eye and identify a screen in the reflection. The identification may include generating a mask that includes the reflection and applying the mask to eye image 510 of the eye to generate screen image 520 (i.e., output image). In other words, the U-net neural network may be configured to predict whether a screen appears in the eye image and if so, where the screen is located (i.e., a central position of the screen) in the eye image.

Figure 6:
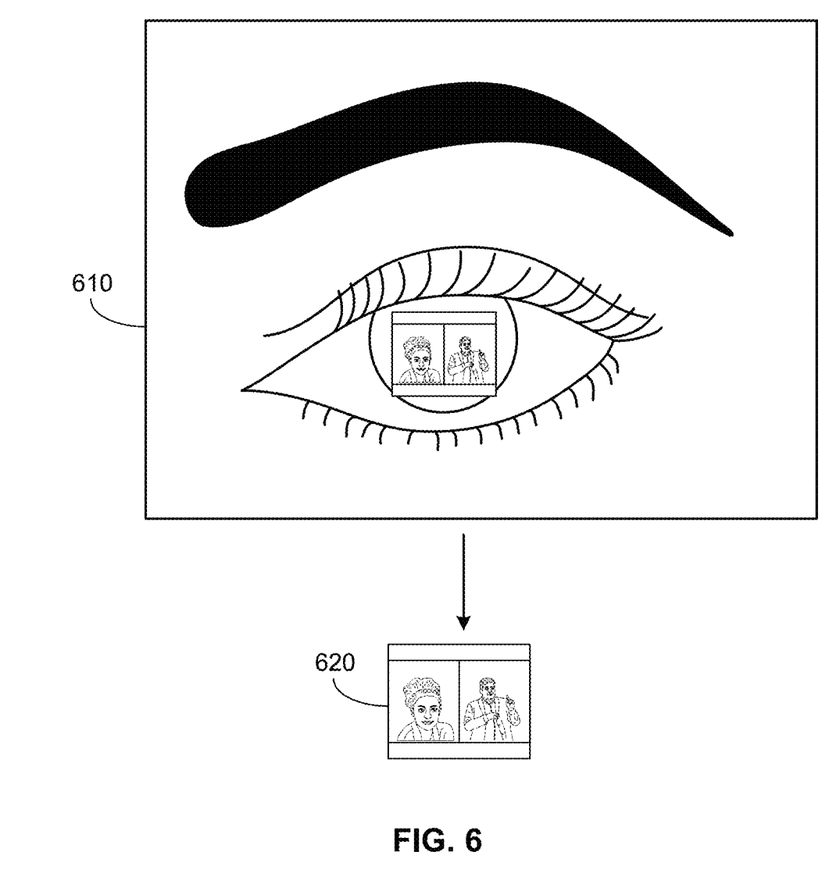
FIG. 6 illustrates a screen image identified in a reflection in an eye image according to a possible implementation of the present disclosure.

FIG. 6 illustrates a screen image identified in a reflection in an eye image according to a possible implementation of the present disclosure. As shown, a reflection can be detected in the eye image 610. A screen can be identified in the reflection by a neural network to generate a screen image 620. In this possible implementation, the screen is the entire reflection. In other words, a screen image 620 can be generated by masking (i.e., segmented) the eye image 610 based on the results of the U-net neural network 500 (see FIG. 5), which is configured to locate the screen in the image.

Returning to FIG. 4, the lower-power mode 600 process described above may be repeated periodically (i.e., cycled) to track the screen in subsequently captured images to determine the screen time for an instance of screen viewing. Determining the screen time of an instance may include determining when the screen timer 430 should be stopped (i.e., deactivated, turned OFF). For example, when it has been determined that no screen has been detected in the images for a number of cycles, the screen timer may be turned OFF. Each cycle may be separated by a cycle period. For example, the lower-power mode may be repeated with a cycle period of every few seconds (e.g., 5 seconds). The cycle period for the lower-power mode may be longer than the cycle period of the higher-power mode to conserve power. The cycle period may be selected as a balance between screen time accuracy and power consumption. In a possible implementation, the lower-power mode 600 may be a default mode of the method.

As shown in FIG. 4, the method 400 may include a no-camera mode 900. The no-camera mode 900 uses the location/orientation sensors 443 of the head-mounted device to determine orientation data of the user and relative location data of a device. The orientation data of the user and the relative location data of the device (i.e., the screen) may be analyzed by a machine learning model 444 to determine that a screen-viewing condition (i.e., viewing condition) exists. For example, a viewing condition may exist when the orientation of the head-mounted device is pointed in a direction of a device having a screen. The detection of the viewing condition may trigger the screen timer 430 to start timing. As mentioned previously, the relative location data may include a range and an angle computed based on using ultra-wideband (UWB) communication. For example, a range between UWB devices may be computed based on a round trip time of a UWB packet communicated between the UWB devices. Further, an angle between the UWB devices may be computed based on a difference in the times of arrival of the UWB packet at UWB receivers spaced apart on the UWB device receiving the UWB packet.

The no-camera mode 900 process described above may be repeated periodically (i.e., cycled) to track the viewing condition to determine the screen time for an instance of screen viewing. Determining the screen time of an instance may include determining when the screen timer 430 should be stopped (i.e., deactivated, turned OFF). For example, when it has been determined that no viewing condition has been detected in location/orientation data for a number of cycles, the screen timer 430 may be turned OFF. Each cycle may be separated by a cycle period. For example, the lower-power mode may be repeated with a cycle period of every few seconds (e.g., 5 seconds).

As shown in FIG. 4, after a screen time has been computed it may be output for a recording/monitoring 450 process of the method 400. The recording/monitoring process 450 can include recording a screen time determined from the screen timer into a database 750. The recording/monitoring process 450 can further include linking 455 a screen time with a device (i.e., classifying the screen time as for a device). The recording/monitoring process 450 can further include generating 465 an alert based on the screen time or times stored in the database 750. For example, a screen time for an instance may be output from the screen timer in the higher-power mode, lower-power mode, or no-camera mode to be classified, recorded, and evaluated for generating an alert.

Figure 7:
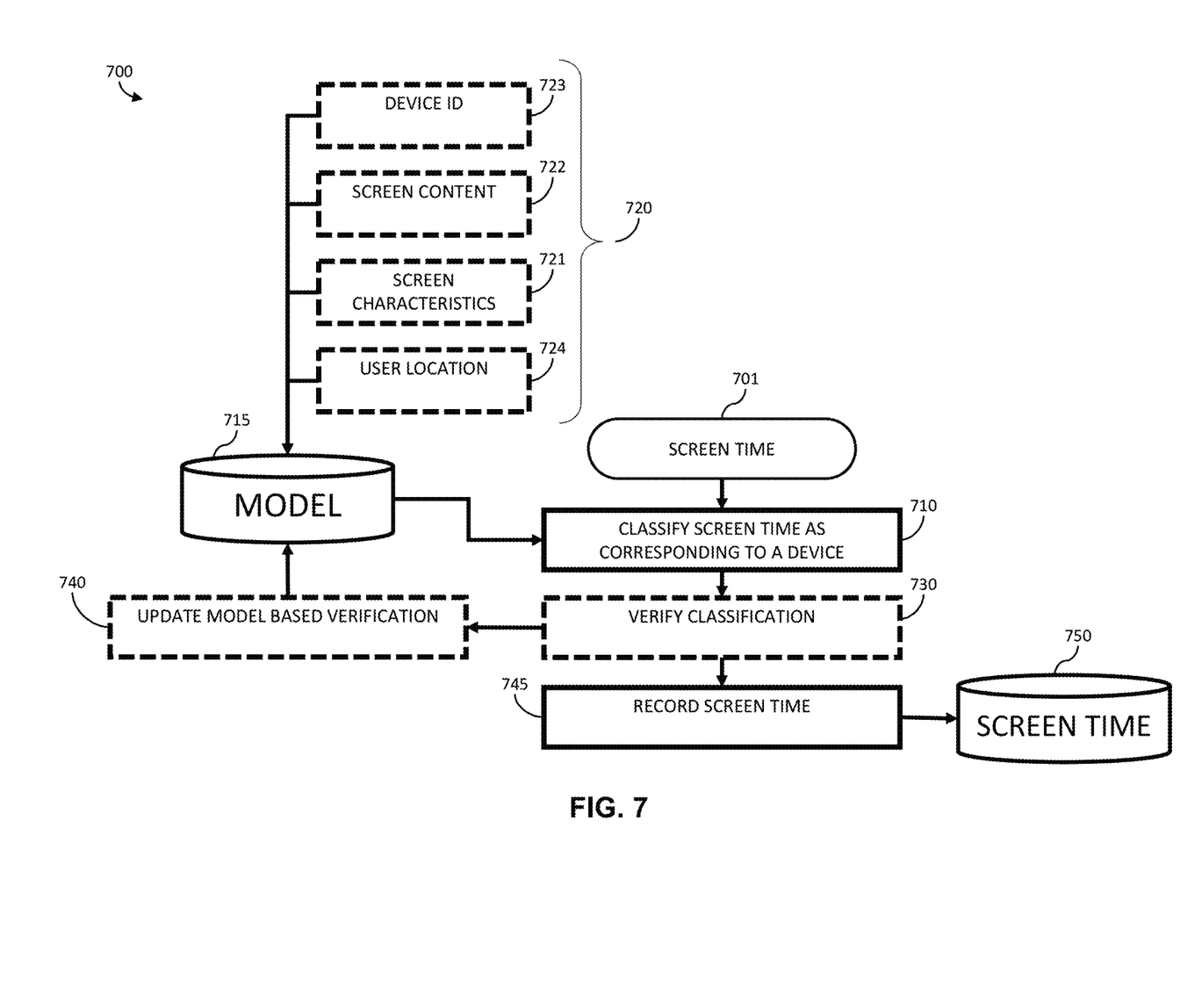
FIG. 7 is a flow chart of a method for recording a screen time according to a possible implementation of the present disclosure.

FIG. 7 is a flow chart of a method for recording a screen time according to a possible implementation of the present disclosure. The method 700 includes receiving a screen time (e.g., of an instance) acquired using the head-mounted device in the higher-power mode, the lower-power mode, or the no-camera mode. The method 700 further includes classifying 710 the screen time as screen time corresponding to a device.

The classifying 710 may utilize a machine learning model 715. The machine learning model 715 may receive device information 720 acquired during the instance to link the screen time 701 with a class of devices (e.g., laptop, desktop, television, etc.) or a particular device (e.g., John's phone, living-room TV, etc.). The device information may affect a confidence of the classification. For example, if a hand is recognized holding the screen in an image, then the model may lower a confidence that the screen is a television and increase a confidence that the screen is a mobile phone or tablet.

The device information 720 can include screen characteristics 721 derived from captured images (e.g., FOV images). In a possible implementation, the screen characteristics 721 include physical or electronic attributes of the screen derived from the image, such as a screen size (e.g., length, width), a screen resolution, or a screen refresh rate. In another possible implementation, the screen characteristics 721 can include attributes of a screen's surroundings derived from the image, such as a housing of the screen, or a hand holding the screen.

The device information 720 can further include screen content 722 derived from captured images (e.g., eye images). In a possible implementation, the screen content may include motion, color, images, or the like that are suggestive of the type of screen being observed. For example, a particular user interface may be recognized and used to determine the device.

The device information 720 can further include a device identification (device ID 723) derived from location data. In a possible implementation, the device ID 723 may include identifying information (e.g., address) that is communicated over a UWB packet. For example, an address communicated in a packet transmitted from a device may be used to determine the device.

The device information 720 can further include a user location 724. The user location can be a location derived from a location service (e.g., GPS, indoor positioning, etc.). The user location 724 may be a room. Knowledge of the room can inform the decision to be made by the machine learning model. For example, a TV is more likely in a living room than a bathroom. In other words, the method may include receiving a location of the head-mounted device; and selecting likely devices based on the location.

The method for recording a screen time may further include verifying 730 that the classification made by the machine learning model 715 was correct or incorrect. The verification may be carried out in a variety of ways. In one possible implementation, an image from the front-facing camera may be captured (e.g., during a lower power mode). The FOV image may be analyzed to determine if the classification of the device was correct. In another possible implementation, the verification may include querying the user to classify the device (e.g., when no results from the model are returned) or validate that classification was correct. The result of the verification may be used to update the model 740. For example, updating 740 the model may include adjusting the model so that confidence levels for classifications resulting from certain device information 720 change based on instances of verification or based on rates of verifications (e.g., false identification rate, true identification rate).

The method for recording a screen time may further include recording the (classified) screen time in a database 750. The recording may include updating (i.e., increasing) a screen time for a device by the screen time 701 received (or derived) from the screen timer. Accordingly, the recording 745 may include querying the database for an entry corresponding to a device and then adding the screen time for the device to the entry or creating a new entry for the device.

Returning to FIG. 4, the multi-mode screen-time tracking method 400 may further include generating an alert based on the screen times recorded in the database 750 and transmitting the alert to a display of the head-mounted device. Generating the alert may include querying the database based on one or more rules corresponding to one or more alerts. For example, a rule may state that the screen time of a particular device should not be more than a value during a period. Generating the alert may include querying the database 750 to determine the screen time for the particular device and then comparing the screen time to a threshold. If the comparison shows that the screen time for the particular device is at or above the threshold then an alert may be generated. Various alerts may be generated.

The alert may include a message presented to a user regarding the screen time. For example, the message may instruct the user to "take a break" from the use of the device. The alert may include a report of screen time usage for a period (or periods). The alert may include a comparison of a first screen time from a first period to a second screen time from a second period. These types of alerts may be presented to a display of the head-mounted device for a user to observe.

Figure 8:
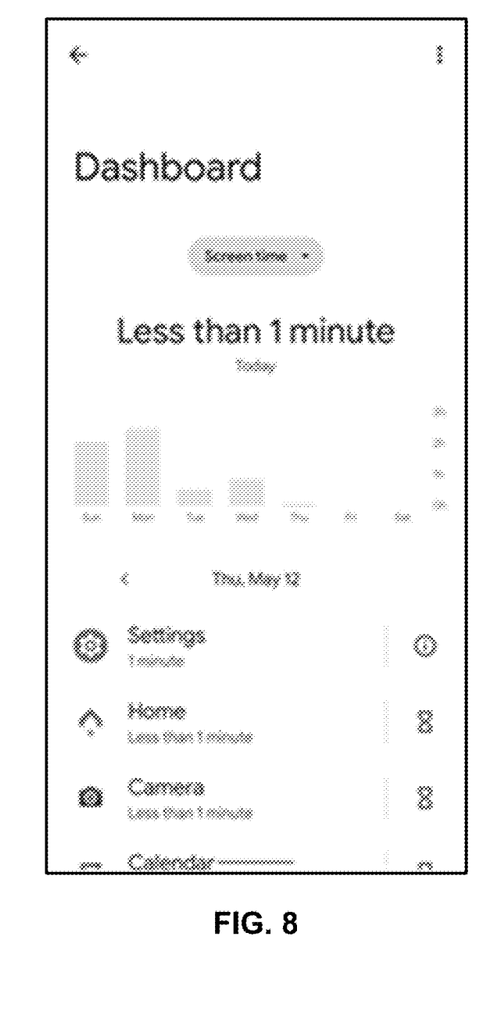
FIG. 8 is an alert generated based on screen time according to a possible implementation of the present disclosure.

FIG. 8 is an example of an alert based on screen times. The alert can include daily screen times for all devices (e.g., a desktop, a phone, a tablet etc.) shown as a bar chart for each day of the week. The alert can further include screen times accumulated for each of the devices over a week. The alert can further include a total screen time for all devices during the week. The alert can further include an analysis of screen time, such as a daily average of screen time. The alert can further include changes in screen times from a previous period (i.e., last week). An alert may be triggered to display at the conclusion of a period (e.g., week) or may be triggered by a user. In some implementations, an alert can be generated when one or more of the screen times satisfy one or more criteria.

In the specification and/or figures, typical embodiments have been disclosed. The present disclosure is not limited to such exemplary embodiments. The use of the term "and/or" includes any and all combinations of one or more of the associated listed items. The figures are schematic representations and so are not necessarily drawn to scale. Unless otherwise noted, specific terms have been used in a generic and descriptive sense and not for purposes of limitation.

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. The terms "optional" or "optionally" used herein mean that the subsequently described feature, event or circumstance may or may not occur, and that the description includes instances where said feature, event or circumstance occurs and instances where it does not. Ranges may be expressed herein as from "about" one particular value, and/or to "about" another particular value. When such a range is expressed, an aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

Some implementations may be implemented using various semiconductor processing and/or packaging techniques. Some implementations may be implemented using various types of semiconductor processing techniques associated with semiconductor substrates including, but not limited to, for example, Silicon (Si), Gallium Arsenide (GaAs), Gallium Nitride (GaN), Silicon Carbide (SiC) and/or so forth.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the implementations. It should be understood that they have been presented by way of example only, not limitation, and various changes in form and details may be made. Any portion of the apparatus and/or methods described herein may be combined in any combination, except mutually exclusive combinations. The implementations described herein can include various combinations and/or sub-combinations of the functions, components and/or features of the different implementations described.

It will be understood that, in the foregoing description, when an element is referred to as being on, connected to, electrically connected to, coupled to, or electrically coupled to another element, it may be directly on, connected or coupled to the other element, or one or more intervening elements may be present. In contrast, when an element is referred to as being directly on, directly connected to or directly coupled to another element, there are no intervening elements present. Although the terms directly on, directly connected to, or directly coupled to may not be used throughout the detailed description, elements that are shown as being directly on, directly connected or directly coupled can be referred to as such. The claims of the application, if any, may be amended to recite exemplary relationships described in the specification or shown in the figures.

As used in this specification, a singular form may, unless definitely indicating a particular case in terms of the context, include a plural form. Spatially relative terms (e.g., over, above, upper, under, beneath, below, lower, and so forth) are intended to encompass different orientations of the device in use or operation in addition to the orientation depicted in the figures. In some implementations, the relative terms above and below can, respectively, include vertically above and vertically below. In some implementations, the term adjacent can include laterally adjacent to or horizontally adjacent to.

The invention claimed is:

1. A computer-implemented method, comprising:
    capturing an eye image of an eye using an eye-tracking camera of a head-mounted device, the eye image being an image of a surface of the eye of a user wearing the head-mounted device;
    analyzing the eye image to identify a screen reflection, the screen reflection corresponding to a screen that is positioned in front of the user and reflecting off the surface of the eye of the user;
    starting a screen timer after the screen reflection is identified;
    tracking the screen reflection over time; and
    stopping the screen timer when the screen reflection is no longer identified.

2. The computer-implemented method according to claim 1, wherein the tracking the screen reflection over time includes repeating the capturing and the analyzing at a cycle period to periodically capture subsequent eye images to track the screen reflection over time.

3. The computer-implemented method according to claim 2, wherein the cycle period is greater than 2 seconds.

4. The computer-implemented method according to claim 2, wherein the cycle period is less than 2 seconds.

5. The computer-implemented method according to claim 1, further comprising detecting that the head-mounted device is in a lower-power mode for screen time tracking, wherein the detecting the lower-power mode includes:
    detecting a battery level of the head-mounted device; and
    determining that the battery level is below a threshold.

6. The computer-implemented method according to claim 1, wherein analyzing the eye image to identify the screen reflection includes:
    applying the eye image to an input of a neural network, the eye image including the eye and the screen reflection; and
    receiving a screen image at an output of the neural network, the screen image including the screen reflection.

7. The computer-implemented method according to claim 1, further including:
   detecting that the head-mounted device is in a higher-power mode for screen time tracking;
   capturing a field-of-view image using a front facing camera of the head-mounted device;
   analyzing the field-of-view image to identify the screen;
   starting the screen timer after the screen is identified;
   periodically capturing subsequent field-of-view images to track the screen over time; and
   stopping the screen timer when the screen is no longer identified in the subsequent field-of-view images.

8. The computer-implemented method according to claim 7, wherein detecting that the head-mounted device is in the higher-power mode for the screen time tracking includes:
   detecting a battery level of the head-mounted device; and
   determining that the battery level is above a threshold.

9. The computer-implemented method according to claim 7, further including:
   detecting that the head-mounted device is in a no camera mode for the screen time tracking;
   capturing orientation data of the head-mounted device using at least one orientation sensor of the head-mounted device;
   capturing relative location data of a device from an ultra-wideband (UWB) signal received at the head-mounted device;
   analyzing the orientation data and the relative location data to determine a viewing condition;
   starting the screen timer after the viewing condition is identified;
   periodically capturing subsequent orientation data and relative location data to track the viewing condition over time; and
   stopping the screen timer when the viewing condition can no longer be tracked.

10. The computer-implemented method according to claim 9, further including:
   recording a screen time in a database based on the screen timer; and
   generating an alert when the screen time satisfies a criterion.

11. The computer-implemented method according to claim 10, further including:
   classifying instances of screen times as corresponding to devices based on device information captured by the head-mounted device.

12. A head-mounted device comprising:
   an eye-tracking camera; and
   a processor in communication with the eye-tracking camera, the processor configured to by software instructions to:
      receive an eye image of an eye from the eye-tracking camera, the eye image being an image of a surface of the eye of a user wearing the head-mounted device;
      analyze the eye image to identify a screen reflection, the screen reflection corresponding to a screen that is position in front of the user and reflecting off the surface of the eye of the user;
      start a screen timer after the screen reflection is identified;
      track the screen reflection over time; and
      stop the screen timer when the screen reflection is no longer identified.

13. The head-mounted device according to claim 12, wherein the processor is further configured by software instructions to:
   repeatedly receive and analyze at a cycle period to periodically capture subsequent eye images to track the screen reflection over time.

14. The head-mounted device according to claim 12, wherein the processor is further configured by software instructions to:
   determine that a battery level of the head-mounted device is below a threshold; and
   detect that the head-mounted device is in a lower-power mode for screen time tracking based on the determination.

15. The head-mounted device according to claim 12, wherein the processor is further configured by software instructions to:
   apply the eye image to an input of a neural network, the eye image include the eye and the screen reflection; and
   receiving a screen image at an output of the neural network, the screen image including the screen reflection.

16. The head-mounted device according to claim 12, wherein the processor is further configured by software instructions to:
   detect that the head-mounted device is in a higher-power mode for screen time tracking;
   capture a field-of-view image using a front facing camera of the head-mounted device;
   analyze the field-of-view image to identify the screen;
   start the screen timer after the screen is identified;
   periodically capturing subsequent field-of-view images to track the screen over time; and
   stop the screen timer when the screen is no longer identified in the subsequent field-of-view images.

17. The head-mounted device according to claim 16, wherein the processor is further configured by software instructions to:
   determine that a battery level of the head-mounted device is above a threshold; and
   detect that the head-mounted device is in a higher-power mode for the screen time tracking based on the determination.

18. The head-mounted device according to claim 16, wherein the processor is further configured by software instructions to:
   detect that the head-mounted device is in a no camera mode for the screen time tracking;
   receive orientation data of the head-mounted device from at least one orientation sensor of the head-mounted device;
   receive relative location data of a device from an ultra-wideband (UWB) signal received at the head-mounted device;
   analyze the orientation data and the relative location data to determine a viewing condition;
   start the screen timer after the viewing condition is identified;
   periodically receive subsequent orientation data and relative location data to track the viewing condition over time; and
   stop the screen timer when the viewing condition can no longer be tracked.

19. The head-mounted device according to claim 18, wherein the processor is further configured by software instructions to:
   record a screen time in a database based on the screen timer; and
   generate an alert when the screen timer satisfies a criterion.

20. The head-mounted device according to claim 19. wherein the processor is further configured by software instructions to:
  classify instances of screen times as corresponding to devices based on device information captured by the head-mounted device.

* * * * *